Figure 1:
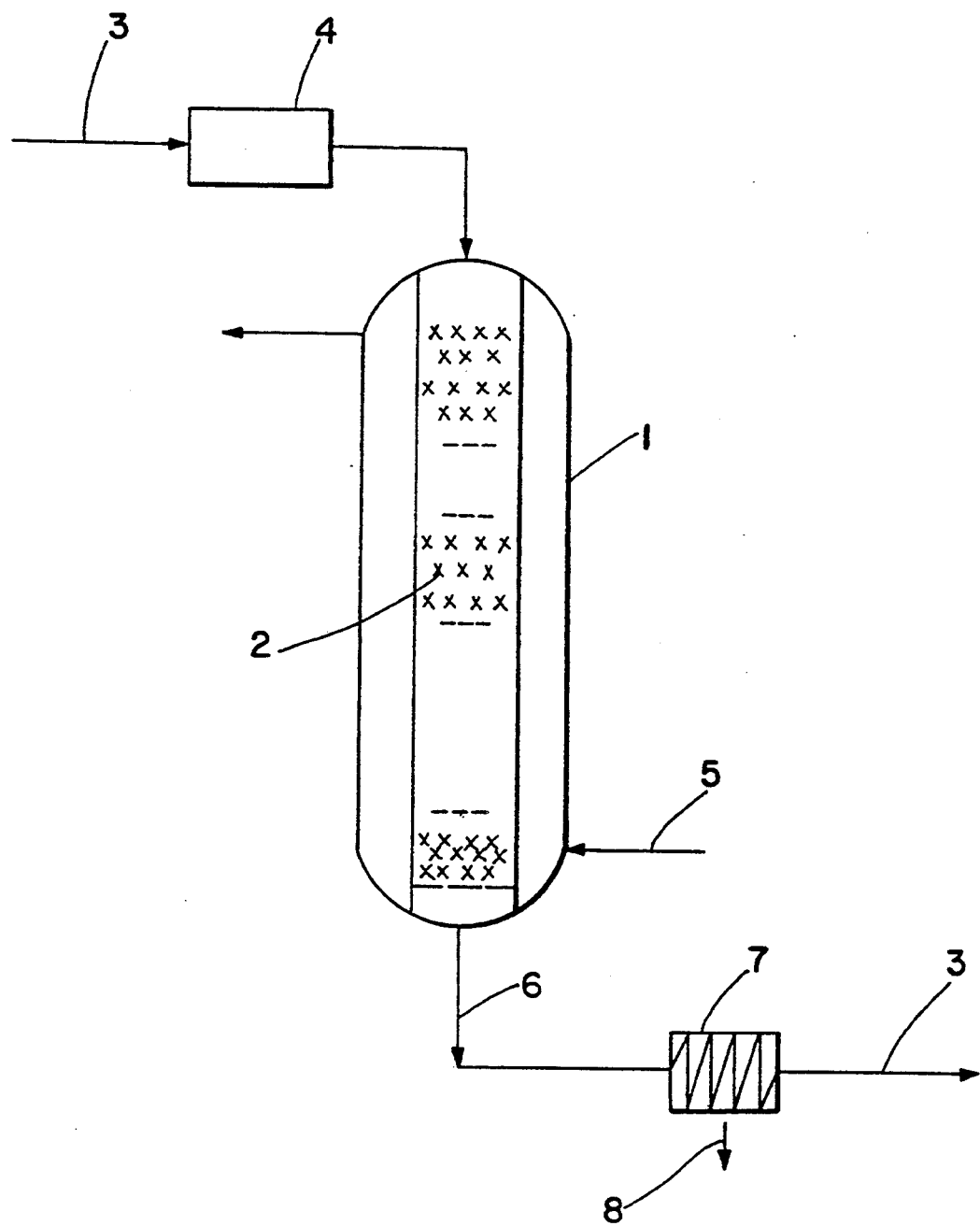

United States Patent [19]

Sipos et al.

[11] Patent Number: 5,371,221
[45] Date of Patent: Dec. 6, 1994

[54] PROCESS FOR RECOVERY OF CAFFEINE FROM ACTIVATED CARBON

[75] Inventors: Stefan Sipos, Bremen, Germany; Gary Jones, Stettlen, Switzerland

[73] Assignee: Jacobs Suchard AG, Zurich, Switzerland

[21] Appl. No.: 92,339

[22] Filed: Jul. 15, 1993

[30] Foreign Application Priority Data

Jul. 31, 1992 [XH] Hague Agreement ......... 92113069.6

[51] Int. Cl.$^5$ ............................................. C07D 473/12
[52] U.S. Cl. ................................... 544/275; 544/274
[58] Field of Search ................................. 544/275, 274

[56] References Cited

U.S. PATENT DOCUMENTS 4,673,743  6/1987  Wilkens ................................ 544/275

Primary Examiner—Nicholas Rizzo
Attorney, Agent, or Firm—Thomas A. Marcoux; Thomas R. Savoie

[57] ABSTRACT

The invention relates to a process for recovering caffeine from caffeine-loaded activated carbon using a circulated inert gas sweeping stream held at a temperature of 250° to 460° C., in which process the activated carbon is preheated prior to the desorption of the caffeine with heat sources other than the sweeping gas and held during the desorption step at a uniform temperature or at a temperature increasing from the inlet to the outlet of the inert gas sweeping stream within the range of 250° to 460° C. and the caffeine is subsequently separated from the inert gas sweeping stream by conventional means.

9 Claims, 2 Drawing Sheets

PROCESS FOR RECOVERY OF CAFFEINE FROM ACTIVATED CARBON

The present invention relates to a-process for recovery of caffeine from caffeine-loaded activated carbon.

With a number of decaffeination processes for vegetable products, including coffee, activated carbon is used at some stage for selective separation of the caffeine. Because the caffeine obtained as a by-product can be used for other purposes, efforts are made to separate the caffeine from the activated carbon by economical means.

The desorption of the caffeine from the activated carbon is not easy because activated carbon is a very good adsorbent for caffeine. U.S. Pat. No. 4,673,743 to Wilkens describes a process for separating caffeine from caffeine-loaded activated carbon with which a circulated inert gas sweeping stream is passed rectangularly through the activated carbon at a temperature of 350° to 450° C., and the caffeine desorbed from the activated carbon is precipitated by cooling in the form of solid particles and separated. It is disadvantageous with that process that the activated carbon layer thickness or bed depth cannot be more than 60 mm. If the layer thickness is increased, the caffeine yield decreases considerably. It is pointed out on column 2, line 52 of the Wilkens Patent that layer thicknesses from 20 to 60 mm have proven to be useful. The process cannot be carried out in an economic manner with such layer thicknesses, and that is also the reason why that process has hitherto not been used in practice.

It is the object of the present invention to make available a process for recovering caffeine from caffeine-loaded activated carbon with which substantially greater activated carbon bed depths can be used and, nevertheless, high caffeine yields can be achieved. Due to greater activated carbon bed depths, larger amounts of activated carbon can be treated per unit of time while employing lower amounts of sweeping gas. Such a process thereby becomes essentially more economical.

It has been found within the present invention that a thorough and even preheating of the caffeine-loaded activated carbon to within the desorption temperature range permits the successful use of significantly deeper beds for desorption. The deeper beds reduce the time and the quantity of hot gas or steam required per unit of carbon desorbed, thereby making the entire process economically attractive.

The present invention therewith relates to a process for recovering caffeine from caffeine-loaded activated carbon with the aid of a circulated inert gas sweeping stream held at a temperature of 250° to 460° C., and which is characterized in that the activated carbon is preheated prior to the desorption of the caffeine and held during the desorption step at a uniform temperature or at a temperature increasing from the inlet to the outlet of the inert gas sweeping stream within the range of 250° to 460° C. and the caffeine is subsequently separated from the inert gas sweeping stream by conventional means. The preheating preferably takes place at a temperature of at least 250° C., especially at least 320° C. The sweeping gas is preferably fed countercurrent to carbon in continuous systems.

A fixed or moving carbon bed is preheated by heat sources other than the sweeping gas. With fluidized carbon beds, the external heat sources are not necessarily required but preferred.

The carbon bed temperature uniformity or any other selected temperature profile is maintained in the case of fixed or moving carbon beds by external heat sources other than and additional to the sweeping gas. The same is preferred for fluidized beds even if not absolutely necessary.

With a preferred embodiment of the process, the activated carbon is first heated to a temperature of 200° to 250° C. in order to evaporate water present. It is preferred to simultaneously eliminate the air/oxygen content of the activated carbon with a sweeping gas stream. The activated carbon is then subsequently preheated to a temperature within the range of 250° bis 460° C.

The advantage of the process of the invention over that known from the U.S. Patent to Wilkens resides in that the activated carbon bed depth can be more than 6 cm. It is preferably more than 10 cm and especially more than 20 cm and can be up to a few meters.

The process is preferably carried out under slight pressure above atmospheric in order to prevent the infiltration of oxygen.

The drawings show in

Figure 2:
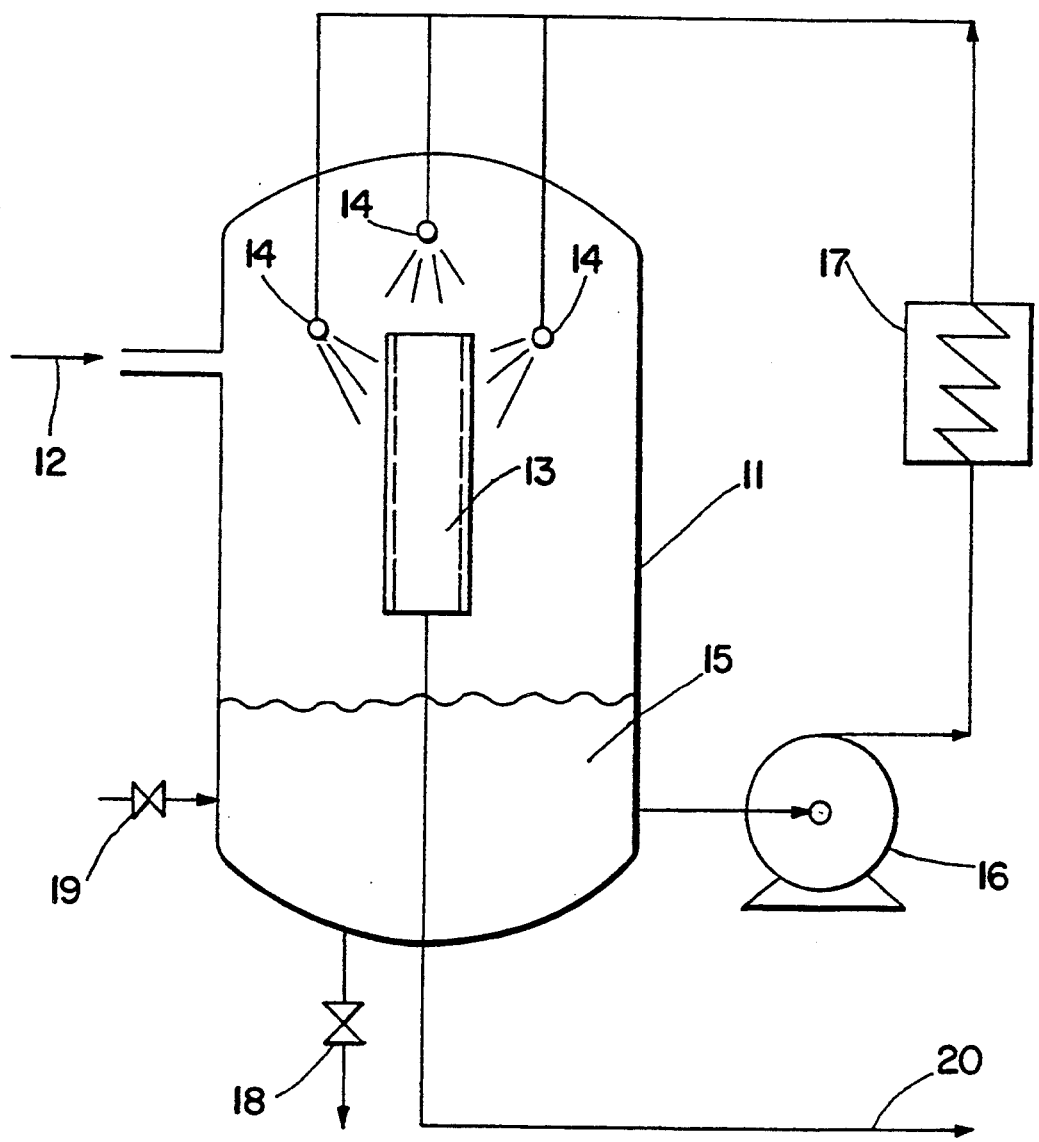

FIG. 1 the schematic representation of an apparatus for carrying out the desorption step of the process of the invention batchwise (a corresponding continuous system would have carbon flowing down and sweeping gas flowing up, i.e. preferably be a countercurrent system) and FIG. 2 a schematic representation of an apparatus for separating the caffeine from the inert gas stream.

Within the process of the present invention, the caffeine-loaded activated carbon is first dried and heated in a conventional way, for example in a vibrating heated surface device. Water leaves the carbon easily at temperatures around 100° C. Heating can be carried out without any special care to reduce air/oxygen up to a temperature between 200° C. and 250° C.—which may depend on the type of carbon. For coconut shell activated carbon, the maximum heating temperature (i.e. without significant caffeine desorption or decomposition occurring, even in the presence of oxygen) has been determined to be 240° to 250° C. This step is important to significantly reduce the overall heat input needed later to preheat the carbon evenly to a sublimation temperature.

The carbon is then introduced into the desorption vessel 1—if not already there—where the oxygen is eliminated with steam or inert gas if this has not already been done simultaneously with the heating step as mentioned above.

The temperature of the carbon bed 2 is subsequently increased to the intended desorption temperature by a heat source independent of the inert gas sweeping stream 3. This can be achieved by heating the walls of the desorption vessel 1 with, for example, a hot medium 3 as shown in FIG. 1 or by heating rods, which are disposed within the desorption vessel 1, but can also be achieved with the use of microwaves, induction heating, etc. It has to be noted here that since a packed fixed or moving bed of activated carbon is a poor heat conductor, relatively small distances to heating elements are highly recommendable, for example 1 to 15, preferably 1 to 10 and especially 2 to 5 cm. The use of finned elements is most preferred. While local overheating is to be avoided, the heating elements are preferably thermostatic (for example by means of ultrahigh-temperature heat transmission oil, fused salts or electrical).

A variant of the process of the invention with which the inert gas sweeping stream 3 can be used for preheating the carbon bed 2 without an external heating device being needed resides in the use of a fluidized carbon bed 2. It is possible due to the fluidizing of the carbon particles to provide for a uniform desorption temperature in the carbon bed 2 so that it is sufficient in that case to preheat the carbon bed only with the inert gas sweeping stream 3. With the use of a fluidized bed, the apparatus of FIG. 1 would have to be modified with the sweeping gas flowing up. The inert gas sweeping stream 3 is also sufficient for maintaining a uniform temperature during the desorption of the caffeine. External heating devices are therefore not absolutely necessary but would in any case improve recovery and are therefore recommendable. On the other hand, in the case of a fixed or moving carbon bed 2, external heating devices are always necessary.

The minimum useful desorption temperature depends on the type of activated carbon used and is in the range of 250° to 340° C. It has been determined for coconut shell-based activated carbon that the minimum useful desorption temperature is between 300° and 320° C. Preheating continues up to ideal working temperatures, which are in the range of about 360° to 430° C. Higher temperatures will accelerate the desorption (i.e. reduce the carbon residence time needed) considerably up to a point where thermal caffeine decomposition starts. Maximum working temperatures are at about 450° to 460° C. Possible working temperatures will therefore be between 250° and 460° C. Some gas stream operation during the preheating phase will help to accelerate reaching the desired uniform working temperature by aiding in distributing the heat from the external source.

It is of decisive importance for the successful operation of the process of the invention that a uniform temperature prevails within the carbon bed 2, it being possible that the bed temperature increases from the inlet of the inert gas sweeping stream 3 into the desorption vessel 1 to the outlet of the caffeine-loaded inert gas sweeping stream 6.

As soon as the desired desorption temperature is reached in the carbon bed 2, the inert gas sweeping stream is turned on and brought to at least that temperature by the heating device 4.

The sweeping gas can be superheated steam or any inert gas. Especially carbon dioxide and nitrogen are suitable. Mixtures of the two as are obtained by combustion can also be used successfully. Furthermore, air whose oxygen content has previously been converted to CO and $CO_2$, preferably by reaction with activated carbon, can also be used as sweeping gas.

The flow velocity of the inert gas sweeping stream 3 is not critical. In the case of a fixed bed or a so-called moving bed, the velocity must be at least so high that the desorbed caffeine is discharged. However, the velocity is preferably so high that a turbulent flow is produced. Linear gas velocities in the order of 0.2 and 0.5 m/sec are preferred. When using a fluidized bed, the gas velocity must be at least so high that a stable fluidized bed is produced.

The working pressure under which the desorption takes place is not critical. Working is, however, preferably either with slight pressure above atmospheric in order to prevent the infiltration of oxygen or with special equipment under vacuum in order to take advantage of higher linear velocities of the sweeping gas possible under such conditions.

The residence time in the desorption vessel 1 of the activated carbon to be desorbed is in the order of 10 mins to 24 hrs, depending on desorption temperatures and bed depths used. Residence times of 30 mins to 10 hrs are preferred, especially 30 mins to 3 hrs, when working temperatures used are between 360° and 430° C. in continuous systems.

The caffeine-loaded inert gas sweeping stream 6 exits from the desorption vessel 1 and is freed of the caffeine in a caffeine separation vessel 7 and then recirculated. The desired caffeine solution 8 is removed from the caffeine separation vessel 7.

The caffeine can be separated from the caffeine-loaded inert gas sweeping stream 6 by known means. Description is given in the U.S. Patent of Wilkens of various processes which can also be used within the scope of the present invention. First, any entrained carbon particles must be removed before the loaded inert gas sweeping stream 6 can be cooled. This can be accomplished by a simple cyclone or a simple filter. The only precaution to be taken is to avoid any cooling of the loaded inert gas sweeping stream 6 because the sublimed caffeine will readily condense or be adsorbed. The caffeine can be separated from the loaded inert gas sweeping stream 6 in a simple manner by condensation as far as the inert gas used is condensable and the caffeine is soluble in it, as, for instance, in the case of superheated steam. On the other hand, if the inert gas is not condensable, a certain quantity of caffeine can be removed from the inert gas sweeping stream 6 by cooling, which causes the caffeine to condense, followed by a simple solid-gas separation device which can be easily made or is readily available from commercial sources (normally a cyclone or a simple filter). Cooling can be accomplished by simple heat transfer, whereby the caffeine can be collected as solids or by injecting water as a spray which then yields the caffeine as a solution. Fiber deep bed filters and wet electrostatic separators can be used to remove finely dispersed caffeine from a non-condensable inert gas. A preferred apparatus for separating the caffeine is shown in FIG. 2 in which the reference numerals have the following meanings: 11 caffeine separation vessel, 12 inert gas sweeping stream loaded with caffeine, 13 sintered metallic filter, 14 filter washing sprays, 15 caffeine solution, 16 recirculating pump, 17 heat exchanger (cooler), 18 caffeine solution drainage, 19 make-up water and 20 the inert gas sweeping stream freed of caffeine and which is recirculated to the desorption zone.

The process of the invention can be carried out as a batch or continuous process. As already mentioned, the process can be carried out with a fixed carbon bed, a moving carbon bed or a fluidized carbon bed. Even vibrating or tumbling bed systems are possible.

The process of the invention has the quite considerable advantage over the prior art according to the U.S. Patent to Wilkens that substantially greater bed depths can be used. Whereas the bed depth with the process of the Wilkens Patent is restricted to maximum 6 cm, bed depths of up to a few meters can be used according to the invention. The prerequisite for that is the careful observance according to the invention of the temperature control within the bed.

The process of the invention is explained in more detail by means of the following example and comparative example.

EXAMPLE

For the recovery of caffeine from caffeine-loaded activated carbon, an apparatus was used as is set forth in FIG. 1. The diameter of the carbon bed 2 was 3 cm and the bed depth 90 cm. Hot oil at 320° C. was pumped through the jacket of the desorption vessel 1 as heating medium for preheating the activated carbon and maintaining a uniform temperature during the desorption. Superheated steam at a temperature of 320° C. was used as inert gas.

The activated carbon loaded with 17% caffeine was introduced into the desorption vessel and heated to begin with to 250° C. The vessel was purged with superheated steam at 250° C. to remove the oxygen, then subsequently heated very quickly to 320° C. and the removal of the desorbed caffeine then commenced. The residence time was 10 hours. By this means, 64% of the caffeine was able to be recovered. 24% remained on the activated carbon and 12% was lost.

Substantially shorter residence times and a more extensive desorption of the caffeine from the carbon with at least unchanging or higher yields are possible upon increasing the desorption temperature.

Comparative Example

With a desorption vessel 1 similar to that shown in FIG. 1, a test was carried out to recover caffeine from caffeine-loaded activated carbon according to the principle of the process of U.S. Pat. No. 4,673,743. The bed depth was 6 cm—which is quoted in U.S. Pat. No. 4,673,743 as maximum bed depth. Nitrogen gas heated to 380° C. was used as inert gas stream. The residence time was 1 hour. By this means, a total of 43% of the amount of caffeine on the activated carbon was able to be recovered. 18% remained on the activated carbon and 39% was lost.

In a further test, the bed depth was increased to 30 cm. Under the same conditions, only about 4% of the caffeine on the activated carbon was able to be recovered. 33% of the caffeine was lost and 63% remained on the activated carbon.

It is shown by this test that it is not possible with the mode of operation in principle of the process of DE-A-3 511 129 to work with bed depths greater than 6 cm. Only infinitely small percentages of the caffeine on the activated carbon was able to be recovered. The major portion of the caffeine is lost.

I claim:

1. A process for separating caffeine from a caffeine-loaded activated carbon bed having a depth of more than 6 cm with the aid of a circulated inert gas sweeping stream held at a temperature of 250° to 460° C. comprising (1) preheating the activated carbon bed by heat sources other than the sweeping gas to a temperature of between 250° to 460° C. prior to the desorption of the caffeine, (2) maintaining a uniform bed temperature within 250° to 460° C. during desorption with an inert gas sweeping stream or at a temperature increasing from the inlet to the outlet of the inert gas sweeping stream within the range of 250° to 460° C., and (3) then cooling the inert gas stream to precipitate the caffeine.

2. The process of claim 1 wherein the carbon bed temperature uniformity or any other selected temperature profile is maintained with the aid of heat sources other than and additional to the sweeping gas.

3. The process of claim 1 wherein the activated carbon is first heated to a temperature of 200° to 250° C. in order to evaporate water present while at the same time sweeping said bed with a gas stream to reduce the air-/oxygen content of the activated carbon prior to the activated carbon being preheated.

4. The process of claim 1 wherein the bed depth of the activated carbon is more than 10 cm.

5. The process of claim 1 wherein the bed depth of the activated carbon is more than 20 cm.

6. The process of claim 1 wherein the desorption step is carried out at a pressure above atmospheric to prevent infiltration of oxygen.

7. The process of claim 1 wherein the desorption step is carried out under vacuum.

8. The process of claim 1 wherein the residence time of the activated carbon in the desorption step is 30 minutes to 10 hours.

9. The process of claim 8 wherein the residence time is 30 minutes to 3 hours.

* * * * *